US008920366B2

(12) United States Patent
Tanghoej

(10) Patent No.: US 8,920,366 B2
(45) Date of Patent: Dec. 30, 2014

(54) IRRIGATION SYSTEM

(75) Inventor: Allan Tanghoej, Kokkedal (DK)

(73) Assignee: Coloplast A/S, Humlebaek (DK)

( * ) Notice: Subject to any disclaimer, the term of this patent is extended or adjusted under 35 U.S.C. 154(b) by 693 days.

(21) Appl. No.: 12/811,829

(22) PCT Filed: Jan. 21, 2009

(86) PCT No.: PCT/DK2009/050013
§ 371 (c)(1),
(2), (4) Date: Jul. 7, 2010

(87) PCT Pub. No.: WO2009/092380
PCT Pub. Date: Jul. 30, 2009

(65) Prior Publication Data
US 2010/0280491 A1 Nov. 4, 2010

(30) Foreign Application Priority Data

Jan. 21, 2008 (DK) .................................. 2008 00077

(51) Int. Cl.
*A61M 5/14* (2006.01)
*A61M 3/02* (2006.01)
(52) U.S. Cl.
CPC ........... *A61M 3/0262* (2013.01); *A61M 3/0295* (2013.01)
USPC .............................................. 604/80; 604/37

(58) Field of Classification Search
USPC ................................ 604/27, 37, 131, 80, 247
See application file for complete search history.

(56) References Cited

U.S. PATENT DOCUMENTS

| | | | | |
|---|---|---|---|---|
| 1,352,306 A | * | 9/1920 | Mott | ............................. 417/478 |
| 1,484,621 A | | 10/1921 | Bond et al. | |
| 3,398,743 A | | 8/1968 | Shalit | |
| 5,505,707 A | | 4/1996 | Manzie | |
| 2006/0009732 A1 | | 1/2006 | Hardy | |

FOREIGN PATENT DOCUMENTS

| | | |
|---|---|---|
| GB | 1550653 | 8/1979 |
| WO | 2005011776 | 2/2005 |

* cited by examiner

*Primary Examiner* — Kevin C Sirmons
*Assistant Examiner* — Deanna K Hall
(74) *Attorney, Agent, or Firm* — Coloplast Corp., Coloplast A/S; Nick Baumann

(57) ABSTRACT

An irrigation system for irrigation of a body cavity includes a reservoir, with an inlet for pouring liquid into the reservoir, an insertion member defining an insertion end for insertion into a body cavity through a body opening of a human being, the insertion member defining at least one opening, and a liquid tube fluidly connecting the reservoir with the insertion member. The reservoir has front and rear walls formed of a flexible, non-elastic polymer material, with the walls having edges sealed together. The reservoir has an upper liquid chamber and a lower liquid chamber, with the two chambers being separated by a first one-way valve.

15 Claims, 3 Drawing Sheets

IRRIGATION SYSTEM

BACKGROUND OF THE INVENTION

1. Field of the Invention

The present invention relates to an irrigation system and the use of such system with a reservoir fluidly connected to an insertion member for insertion into a body cavity of a human being and a means for pumping liquid contained in the reservoir out through an outlet of the insertion member and into the body cavity. Furthermore, the present invention relates to a method of performing irrigation on a human body by use of the irrigation system.

An irrigation system may, for certain users, be used on a daily basis, depending on the user's need. This is for example the case for people suffering from spinal cord injuries, spinal bifida or multiple sclerosis. The system is used to improve quality of life by preventing constipation, reducing time spent for bowel emptying procedures and increasing independency.

2. Description of the Related Art

A simple system widely used, for instance at hospitals, constitutes a bag that is elevated above the person having the transanal irrigation. The bag is connected to a catheter via a tube, which is inserted through the anus into the rectum. The liquid in the bag is introduced into the person; the difference of height between the person and the bag causes a pressure difference. A drawback of this very simple system is that in order to make the system work the bag must be elevated to a position above the person in order to obtain the wanted pressure difference. In order to achieve the necessary pressure, the reservoir should typically be elevated to a height of 1.2-1.5 meters. It may be difficult to find a place in this height to hang the reservoir and for a disabled person in a wheelchair it may be impossible to reach.

Other systems are disclosed in US2006/0009732. One of the systems is designed to provide a colonic lavage with the capability of providing manually controlled pulsation to the lavage liquid through a manual pump. The manual pump can be a conventional in-line squeeze bulb. In an embodiment, a check valve can be disposed in-line with the supply conduit or the manual pump.

SUMMARY OF THE INVENTION

It is an object of an embodiment of the invention to provide a system that is discrete compared to known systems, a system that can be packed to a small volume.

Furthermore, it is an object of an embodiment of the present invention to provide a simple system that is easy to use.

Moreover, it is an object of an embodiment of the invention to provide a system where the reservoir is pressure free and an elevated position of the reservoir during use is not necessary.

Additionally, it is an object of an embodiment of the invention to provide a system which may be disposed after irrigation whereby the user need not clean the system upon use.

It is yet an object of an embodiment of the invention to provide a system wherein the reservoir has built-in means for pumping fluid out of the reservoir and where the pump means are substantially without inherent resilience such that the pump means are easy to use for people having little strength in their hands or poor hand dexterity.

BRIEF DESCRIPTION OF THE DRAWINGS

The invention is disclosed in more detail with reference to the drawing in which.

DETAILED DESCRIPTION OF THE PRESENT INVENTION

Figure 1:
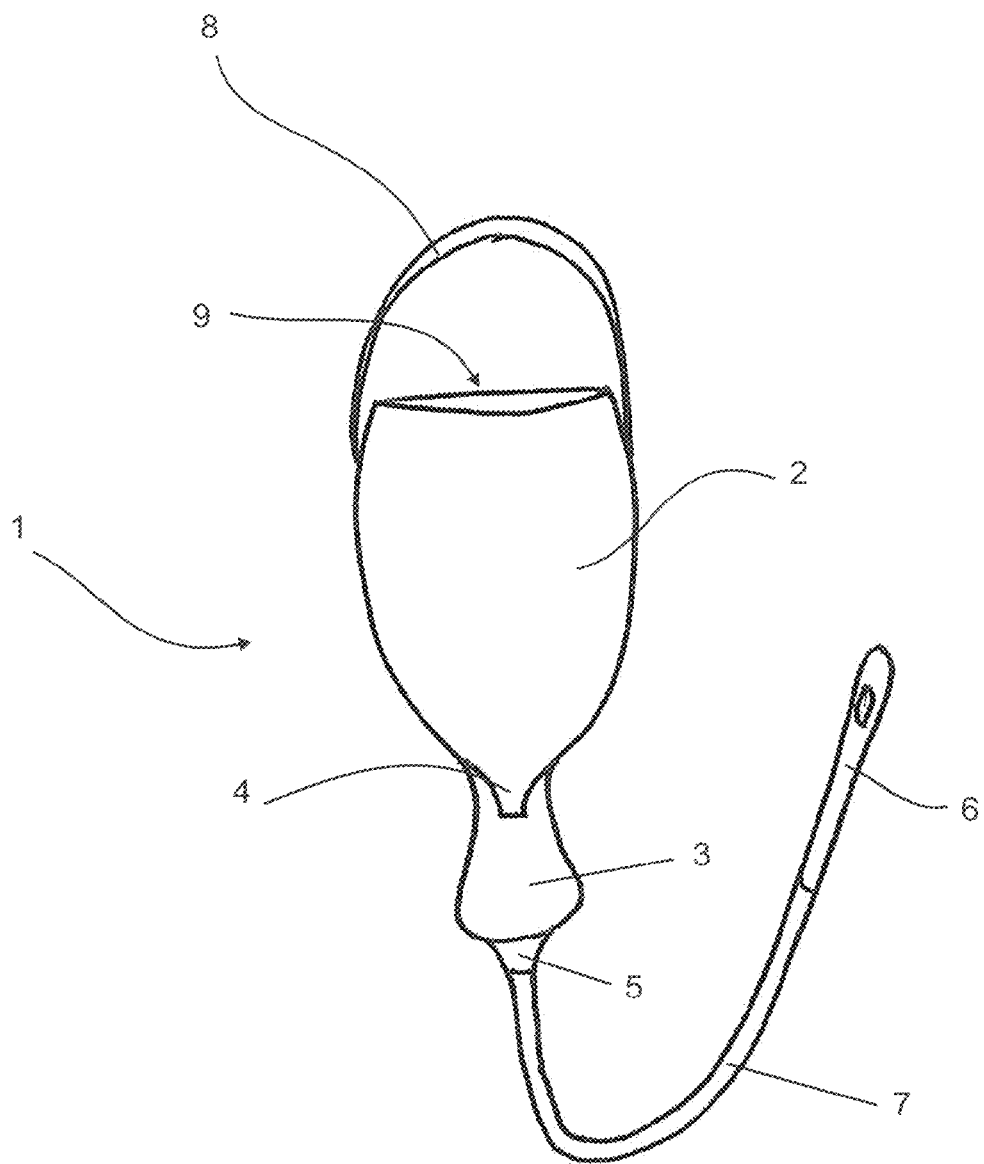
FIG. 1 shows an embodiment of the invention

The invention relates to an irrigation system for irrigation of a body cavity, the system comprising a reservoir with an inlet for pouring liquid into the reservoir, an insertion member defining an insertion end for insertion into a body cavity through a body opening of a human being, the insertion member defining at least one opening, and a liquid tube fluidly connecting the reservoir with the insertion member; wherein the reservoir comprises front and rear walls formed of flexible, non-elastic polymer material, said walls having edges sealed together and the reservoir comprises an upper liquid chamber and a lower liquid chamber, the two chambers being separated by a first one-way valve.

The lower liquid chamber may function as a pump, the one-way valve preventing liquid from flowing from the lower liquid chamber and into the upper liquid chamber. The non-elastic polymer material provides a pump which is filled under the influence of gravity only as it in itself has virtually no resilience and thus cannot be filled by providing a suction force to the upper chamber. The material are typically a polymer film i.e. PVC (Polyvinyle Chloride), PE (Polyethylene), PP (Polypropylene), PA (Polyamide) or thermoplastic elastomers or any sandwich configuration comprising any of the mentioned materials. The lack of resilience (or the non-elasticity) may make it easier to use for people with poor hand dexterity, as they do not have to overcome the resilience of the pump when squeezing it. They only have to provide enough force to squeeze out the liquid, which is relatively easy to do.

The system may be used for irrigation performed to any body cavity such as the uterus, the bowel (the intestinal system) and the bladder.

In the context of the present invention the term "intestinal irrigation" is to be understood as any irrigation/cleaning, by means of a liquid, of any part of the digestive/bowel system between the stomach and the anus. Accordingly, intestinal irrigation comprises irrigation in the rectum, the appendix, the colon and the small intestine, i.e. ileum, jejunum and duodenum. In most embodiments, the system is inserted through the exit of the intestinal system of the user such as a natural anus or artificial anus (a stoma). When inserted through said exit, irrigation liquid may be expelled in an upstream direction of the intestinal system relative to the exit by means of the insertion member.

Irrigation systems are often quite voluminous and difficult to fit into a handbag. Especially for disposable systems, it is desired to provide a system that can be packed into a small volume when not in use and thus have a discrete appearance. In the system of the present invention, the reservoir is prepared from sheets of a non-elastic flexible material and is preferably substantially flat or two-dimensional in empty condition corresponding to a thickness of only a few milimeters such as less than 5 milimeters. This facilitates packing of the system into a small volume, for instance by rolling or folding the reservoir. Apart from being able to fit in a handbag, the compact packaging of the system is also advantageous when the system is disposed, as this can also be done discretely.

In the system of the invention, the irrigation liquid is pumped from the pressure free reservoir directly into the body cavity. The reservoir is not pressurized by pumping gas into the system as in most known systems. The only part of the system being pressurized is the part from the lower chamber to the body cavity.

It is preferred that the first one-way valve is a flap valve. The valve may be a part of the walls of the reservoir, being folded in an appropriate manner to produce a one-way flap valve. Such a valve is easy to produce, being a part of the reservoir wall, and furthermore it is flat and non-voluminous which is desirable for a discrete system.

The reservoir comprises the upper and the lower liquid chambers as an integrated unit and it is prepared by one or more sheets of a non-elastic, flexible material. Thus the reservoir is easy and economic to produce. As an example the reservoir may be produced by welding two sheets of foil or film together along the sides and subsequently welding two pieces of foil to the inner side of the sheets facing each other, such that these two pieces may constitute a foil-valve.

The lower liquid chamber may be filled with liquid from the upper liquid chamber by gravity. When the reservoir is held in a vertical position (upper chamber upwards and lower chamber downwards) and liquid is poured into the upper chamber, the liquid will flow, by gravity, to the lower chamber until this is filled. The position should be vertical, but not necessarily in a higher position than the patient, solving the problem of hanging the reservoir in high and unreachable places known from other products working by gravity. The reservoir of the system of the present invention may be provided with a strap or other fastening means to hold it in position. The strap may facilitate hanging the reservoir over the shoulder or arm of the user.

A second valve may be present between the reservoir and the probe. The valve may preferably be a non-return valve for preventing upstream flow of liquid from the at least one opening towards the reservoir. This prevents contamination of the system for instance by faecal matter or blood present in the body cavity during use.

Such a non-return valve arranged at the end of the liquid tube may additionally or alternatively also be biased in a way that a certain amount of pressure has to be built in the liquid tube/lower chamber before the irrigation liquid can flow out. This prevents irrigation liquid from unintentionally dripping from the liquid tube.

The lower liquid chamber may have a volume being less than 0.5 liter, more preferred less than 0.3 liter and most preferred between 0.09 liters and 0.3 liters. The volume of the lower chamber is adapted to fit the means for applying pressure to it, typically to fit in the hand of the user, but the system may also be operated by other means such as the mouth or an arm, and thus the shape and volume of the chamber may be adapted for this.

The upper chamber may correspond with the ambient air and may thus not be pressurized. The upper chamber may have a volume of between 0.5-2 liters.

The reservoir is provided with an inlet, which may comprise closing means for closing the inlet. The closing means may be a non-return valve allowing liquid to enter the reservoir through the inlet while preventing the liquid from escaping the reservoir through the inlet. Alternatively, or as a supplement, the closing means may comprise a clamp or a screw cap which when fastened to the inlet prevents liquid from flowing into and out of the reservoir through the inlet.

Closing means for the reservoir are optional and not necessary as the upper chamber is not pressurized and the reservoir is held in vertical position during use. However, it may be practical to provide the reservoir with closing means in order not to spill liquid during handling or unintended dropping of the reservoir/system.

A proximal insertion end of the insertion member may define a smooth surface so as to adapt the insertion member to be inserted into a body cavity of a human being, for instance through the anus of the human being.

The insertion member defines at least one opening such as two, three, four or five openings. With respect to the proximal end of the insertion member, the at least one opening is arranged in such a way that when the insertion member is at least partly inserted (e.g. through the artificial/natural anus), the opening(s) is/are positioned in the body cavity, whereby a liquid expelled through the at least one opening is received in said body cavity.

A liquid tube fluidly connects the reservoir and the insertion member, which may be transparent. The tube may comprise a thermoplast such as PVC/PP/PE or a thermoplastic elastomer like a Styrol-Block-Copolymere such as a PUR or a SEBS compound or a cross-linked elastomer like silicone or latex. In one embodiment, the liquid tube takes the form of a foil tube. The sidewalls of the foil tube are movable towards each other and into contact with each other allowing a flat and compact configuration. This is desirable prior to use and after use when the user disposes the system. In the context of the present invention, the term "tube" is to be understood as a conduit defined by a long hollow object (for instance cylindrical) used to hold and conduct liquids. The tube may be extruded as a cylindrical object or it may comprise two foils that are welded together.

In order to prevent the insertion member from slipping out of the body cavity during irrigation, the insertion member may comprise a retaining means for retaining, the insertion member in the body cavity when inserted through the body opening. The retaining means may be changeable between two configurations, a non-retaining configuration allowing the insertion member to be inserted into and retracted from the body opening and a retaining configuration wherein the retaining means prevents retraction of the insertion member when it is inserted into the body cavity through the body opening.

In order to provide a retaining means, which is adapted to define the two positions, the retaining means may comprise a balloon fluidly connected with a balloon pump such that operation of the balloon pump causes the balloon to expand. The balloon may be a gas balloon or a liquid balloon. The gas/liquid pump may be a foil pump. The retaining means may also comprise a conus or other retaining means well-known in the art. The retaining means may be defined on an outer surface of the insertion end.

A further aspect of the invention relates to a method of performing an irrigation of a body cavity of a human being by use of an irrigation system as earlier described, the method comprising the steps of:
  orienting the reservoir in a vertical position,
  filling a liquid into the reservoir via the liquid inlet, at least a part of the liquid passing from the upper chamber to the lower chamber,
  inserting the insertion member into a body cavity via a body opening of a human being,
  applying pressure to the outside of the lower liquid chamber, thereby pumping at least a part of the liquid from the lower chamber to enter into the body cavity and
  retracting the insertion member from the body cavity.

The lower liquid chamber is alternately pressurized thus facilitating a pulsating flow of liquid from the reservoir to the body cavity.

Pressure may be removed from the lower chamber whereby the lower chamber will be filled again with liquid from the upper reservoir before applying pressure again. This step may be repeated until sufficient liquid is pumped into the body cavity. The lower liquid chamber may thus function as a pump for pumping liquid from the reservoir to the body cavity.

The system is independent of hanging the bag, gravity is only needed to pass liquid from the upper to the lower chamber. It is often difficult to handle a pressurized system properly. The present system is easy to understand and easy to handle.

The reservoir is prepared from a flexible, non-elastic material, such as a polymer film and the lower chamber can thus be deformed when the user applies pressure to the walls of the chamber, for instance by grabbing the chamber and squeezing it with the fingers. In this way, the chamber may function as a pump. Between the two chambers is a first one-way valve allowing liquid to pass from the upper chamber to the lower chamber, but not the opposite way.

Preferably, a second one-way valve is present between the insertion member and the reservoir in order to prevent liquid from passing from the insertion member to the reservoir, as this may cause contamination.

The reservoir may be made in one piece or by joining one or more pieces, such as plastic foils/films together for instance by gluing or welding. In one embodiment, at least a part of the reservoir is transparent, in a way that the user can visually determine whether a liquid is present in the reservoir or not. In another embodiment, the entire reservoir is transparent. The reservoir may comprise means for indicating the volume of a liquid contained in the reservoir, such as indications in form of a scale on a sidewall of the reservoir.

The reservoir may have any suitable shape. Typically, the upper chamber is broader than the lower chamber, as the upper chamber typically should be able to contain larger amounts of liquid. Furthermore, the lower chamber is usually smaller as it may be designed to fit in the hand or mouth of the user, or to fit between the knees or under the arm, depending on the way it may be operated. In one embodiment of the invention, the first valve and the lower chamber may be elongated in order to create a distance between the upper chamber and the lower chamber. In this way, the lower chamber may be more easy to reach for the user, for instance when the reservoir is hung over the shoulder or arm of the user.

The inlet of the reservoir may be adapted to allow at least a part of a water tap to be inserted into the inlet, whereby water running from the water tap may flow into the reservoir without spillage. The inlet may comprise means for temporarily fastening the inlet/reservoir to the water tap in a position where water running from the tap fills the reservoir. This allows a user to fill the reservoir by use of one hand, for instance by attaching the reservoir to the water tap by means of a first hand and subsequently opening a valve of the tap by means of the same first hand allowing water to run into the reservoir.

DESCRIPTION OF THE PREFERRED EMBODIMENTS

The invention is now explained in more detail with reference to the drawing showing embodiments of the invention.

In FIG. 1, an embodiment of the invention is shown. The system comprises a reservoir 1, the reservoir comprising an upper liquid chamber 2 and a lower liquid chamber 3, separated by a first one-way valve 4. The upper chamber of the reservoir comprises an inlet 9 for filling liquid into the reservoir. The inlet 9 may be an open portion of the reservoir 1, as shown in FIG. 1, or it may be provided with closing means, e.g. a one-way valve or other sealing means. A first one-way valve 4, allowing liquid to from the upper chamber 2 to the lower chamber 3, but not the other way, separates the upper and lower chambers 2, 3. The lower chamber 3 is communicating with an insertion member 6 by means of a fluid tube 7. Between the insertion member 6 and the lower chamber 3, a second one-way valve 5 is inserted. This valve 5 may be pressure sensitive, thus opening when a predetermined pressure is reached. This predetermined pressure is preferably between 0.05 and 0.1 bar corresponding to 5000-10000 Pa. This facilitates that the valve 5 is closed and liquid is not flowing to and out of the insertion member 6 unless intended, for instance when in use. The reservoir 1 is provided with a strap 8 for hanging the reservoir 1 in a vertical position. The reservoir 1 may be hung over the shoulder of the patient or it may be hung on the bed or a chair.

When conducting irrigation, the reservoir 1 is filled with liquid, for instance water, through the inlet 9 while the reservoir 1 is held in a vertical position (upper chamber 2 up and lower chamber 3 down) and the liquid filled into the upper chamber 2 will then flow, by gravity, to the lower chamber 3. When the lower chamber 3 is filled, excess liquid remains in the upper chamber 2. The insertion member 6 is inserted and secured into the body cavity and then the liquid is pumped from the lower chamber 3 to the body cavity by applying pressure to the walls of the lower chamber 3, for instance by squeezing the chamber 3 by the hand and fingers. When compressed, the lower chamber 3 is fully or partly emptied and the liquid flows to the insertion member 6. When compression ceases, for instance when the hand is opened, the lower chamber 3 is again filled from the upper chamber 2 and a new portion of liquid may be squeezed into the body cavity. This procedure is repeated until sufficient liquid has entered the body cavity. Then, the insertion member 6 is removed and the colon is emptied.

Figures 2, 2A:
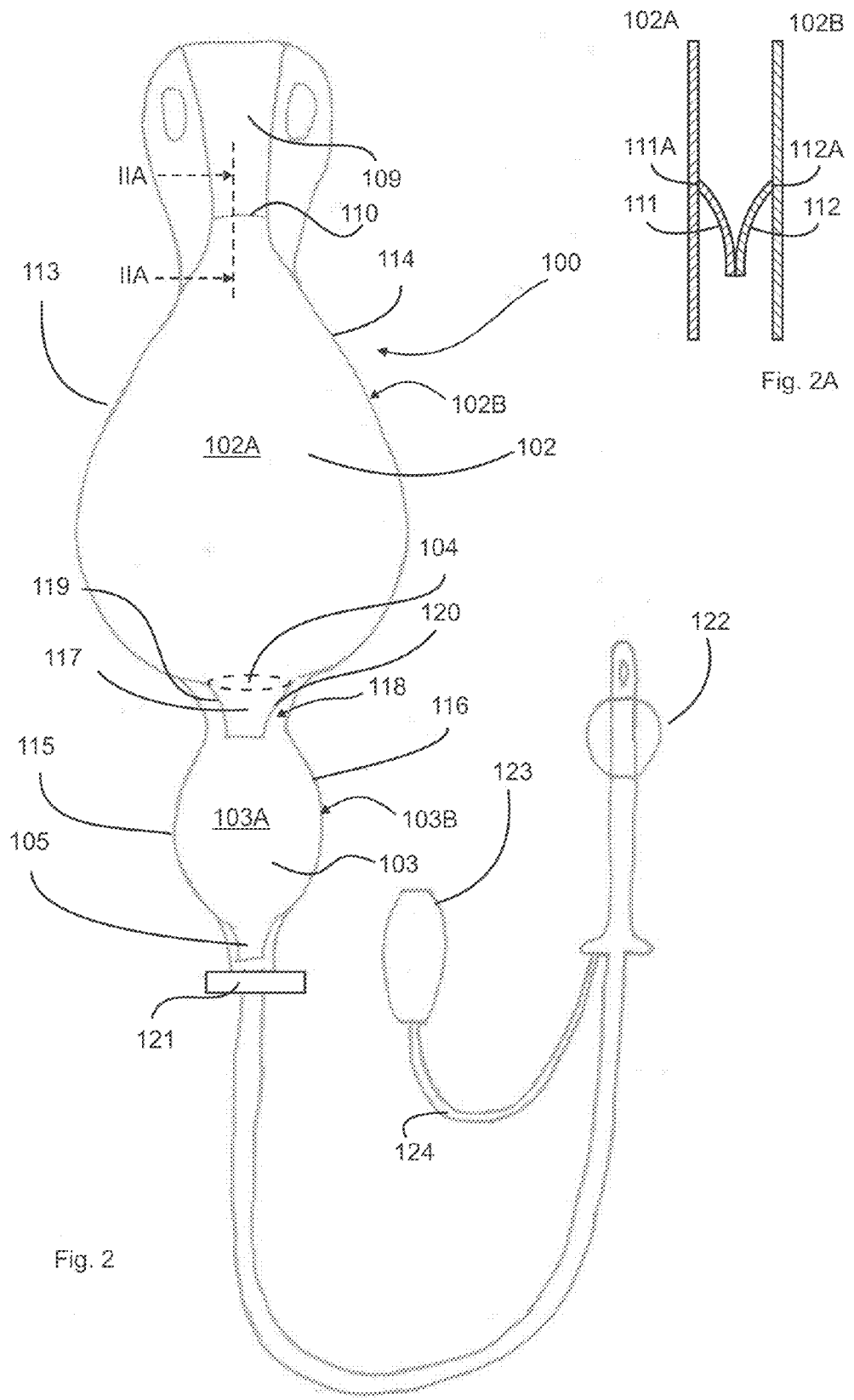
FIG. 2 shows another embodiment of the invention.

FIG. 2 illustrates an embodiment 100 of the invention in which the reservoir has a narrow inlet 109. The inlet may further comprise a one-way valve as indicated at 110. This one-way valve is made as a foil valve or sheet valve as illustrated in FIG. 2A which is illustrating a section along lines II-IIA in FIG. 2. The sheet valve comprises two valve flaps 111 and 112 made of two pieces of foil material, like the remaining reservoir. The size of the two pieces of foil material is selected such that the two pieces of film are able to get in close contact with each other when liquid is not flowing between them. When liquid is flowing they will be separated. The two valve flaps 111 and 112 are welded to the sides of the reservoir at 111A and 112A. The reservoir 101 comprises an upper chamber 102 and a lower chamber 103. The upper chamber comprises two sheets of foil 102A and 102B which are welded together along the sides 113 and 114 to form the chamber. Likewise the lower chamber comprises two sheets of foil 103A and 103B welded together along the sides 115 and 116 to form the lower chamber. The two foils 102A and 103A are in this embodiment constituted by the same sheet of foil and the two foils 102B and 103B are likewise constituted by the same sheet of foil. Thereby the reservoir including the upper and lower chamber is made of two sheets of foil welded together along the sides.

The transition between the upper chamber 102 and the lower chamber 103 is subsequently formed by a one-way valve 104. This one-way valve 104 is in this embodiment made as two pieces of film 117 and 118 welded to the sheets of foil 102A and 102B as indicated at 119 and 120. Thereby these two pieces of film 117 and 118 constitute valve flaps in a foil valve or sheet valve like described in connection with the foil valve or sheet valve at the inlet.

The lower chamber may comprise a one-way valve in form of a foil valve 103 as described in connection with the one-way valve 104. Alternatively the system may comprise a clamp valve 121 well-known in the art.

The insertion member 106 may comprise retention means in form of a balloon 122. This balloon 122 may be inflated under influence of air pumped into it by a pump 123 through a tube 124.

Figure 3:
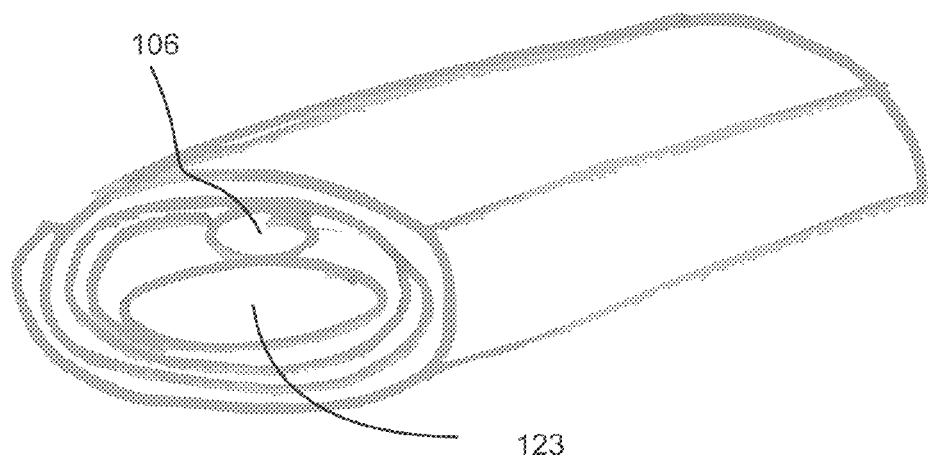
FIG. 3 shows the embodiment of FIG. 2 in a rolled-up configuration.

FIG. 3 illustrates the embodiment of FIG. 2 in rolled-up condition. The entire system 100 may be small enough to fit in a small bag or even in the hand of the user. The pump 122 and the insertion member 106 can be seen in the centre of the rolled-up configuration.

The invention claimed is:

1. An irrigation system for irrigation of a body cavity, the system comprising:
   a reservoir with an inlet for pouring liquid into the reservoir;
   an insertion member defining an insertion end for insertion into a body cavity through a body opening of a human being, the insertion member defining at least one opening; and
   a liquid tube fluidly connecting the reservoir with the insertion member,
   the reservoir including front and rear walls formed of a flexible, polymer film material, said walls having edges sealed together, and
   the reservoir including an upper liquid chamber and a lower liquid chamber configured as an integrated unit and separated by a first one-way valve at an outlet of the upper liquid chamber, with the outlet of the upper liquid chamber and the first one-way valve being enveloped by the lower liquid chamber, and
   with the lower liquid chamber being filled by gravity and configured to function as a pump.

2. The irrigation system according to claim 1, wherein the one-way valve is a flap valve.

3. The irrigation system according to claim 1, wherein the lower liquid chamber is filled with liquid from the upper liquid chamber.

4. The irrigation system according to claim 1, wherein a second valve is present between the reservoir and a probe.

5. The irrigation system according to claim 4, wherein the second valve opens when the pressure from the lower chamber exceeds a predetermined threshold.

6. The irrigation system according to claim 4, wherein the second valve is a non-return valve.

7. The irrigation system according to claim 1, wherein the reservoir is substantially two-dimensional in an empty condition.

8. The irrigation system according to claim 1, wherein the lower liquid chamber has a volume of less than 0.5 l.

9. The irrigation system according to claim 1, wherein the upper chamber is in communication with the ambient air.

10. The irrigation system according to claim 1, wherein the inlet includes a closing element for closing the inlet.

11. The irrigation system according to claim 1, wherein the liquid tube is a foil tube.

12. The irrigation system according to claim 1, wherein the insertion member includes a retaining element for retaining the insertion member in the body cavity when inserted through the body opening.

13. The irrigation system according to claim 1, wherein the reservoir is substantially two-dimensional and packable in an empty condition.

14. A method of performing an irrigation of a body cavity of a human being by use of an irrigation system according to claim 1, the method comprising the steps of:
   orienting the reservoir in a vertical position,
   filling a liquid into the reservoir via the liquid inlet, at least a part of the liquid passing from the upper chamber to the lower chamber,
   inserting the insertion member into the body cavity via the body opening of the human being,
   applying pressure to the outside of the lower liquid chamber thereby forcing at least a part of the liquid from the lower chamber to enter into the body cavity and,
   retracting the insertion member from the body cavity.

15. The method according to claim 14, wherein the lower liquid chamber is alternately pressurized.

\* \* \* \* \*